US00PP31899P2

(12) United States Plant Patent
Detrick et al.

(10) Patent No.: US PP31,899 P2
(45) Date of Patent: Jun. 23, 2020

(54) LILAC PLANT NAMED 'GARLISABZAR'

(50) Latin Name: *Syringa hybrida*
Varietal Denomination: GARlisabzar

(71) Applicant: Early Morning LLC, Greendale, IN (US)

(72) Inventors: Sabrina A. Detrick, Houston, OH (US); Keith W. Zary, Missoula, MT (US)

(73) Assignee: Early Morning LLC, Greendale, IN (US)

( * ) Notice: Subject to any disclaimer, the term of this patent is extended or adjusted under 35 U.S.C. 154(b) by 0 days.

(21) Appl. No.: 16/602,071

(22) Filed: Jul. 30, 2019

(51) Int. Cl.
*A01H 5/02* (2018.01)
*A01H 6/00* (2018.01)

(52) U.S. Cl.
USPC ..... Plt./248
CPC ..... *A01H 6/00* (2018.05)

(58) Field of Classification Search
USPC ..... Plt./248
CPC ..... A01H 5/02
See application file for complete search history.

*Primary Examiner* — Kent L Bell
(74) *Attorney, Agent, or Firm* — Barbara Campbell; Cochran Freund & Young LLC

(57) ABSTRACT

A new and distinct variety of lilac plant having an upright, compact, dense and rounded plant habit, dark colored buds compared to flowers, and having a very strong lilac scent, is disclosed.

4 Drawing Sheets

Genus and species: *Syringa hybrida.*
Denomination: 'GARlisabzar'.

BACKGROUND

'GARlisabzar' is a new and distinct variety of lilac. 'GARlisabzar' originated from a controlled cross in May 2008 in Tipp City, Ohio between the commercial female parent 'Josee' (unpatented), and the commercial male parent, 'Bailsugar' (U.S. Plant Pat. No. 15,588).

The resulting seeds from the cross were collected and planted in Tipp City, Ohio. 'GARlisabzar' was selected in May 2012 from the population of seedlings in Tipp City, Ohio. 'GARlisabzar' was first asexually propagated in May 2013 in Tipp City, Ohio from two-node softwood cuttings rooted under mist at 25 to 27 degrees Celsius.

Other subsequent asexual propagations were conducted in controlled environments in Tipp City, Ohio and demonstrate that 'GARlisabzar' reproduces true to type in successive generations of asexual reproduction via softwood cuttings, tissue culture, and mirco-propagation.

SUMMARY

The following are the most outstanding and distinguishing characteristics of this new variety when grown under normal horticultural practices in Tipp City, Ohio.

1. An upright, compact, dense and rounded plant habit;
2. Dark colored buds compared to flowers; and
3. Having a very strong lilac scent.

DESCRIPTION OF THE PHOTOGRAPHS

This new lilac plant is illustrated by the accompanying photographs which show the plant's overall plant habit including form, foliage, and flowers. The photographs are of a 4-year old plant grown outdoors in Tipp City, Ohio. The colors shown are as true as can be reasonably obtained by conventional photographic procedures.

DETAILED DESCRIPTION

Figure 1:
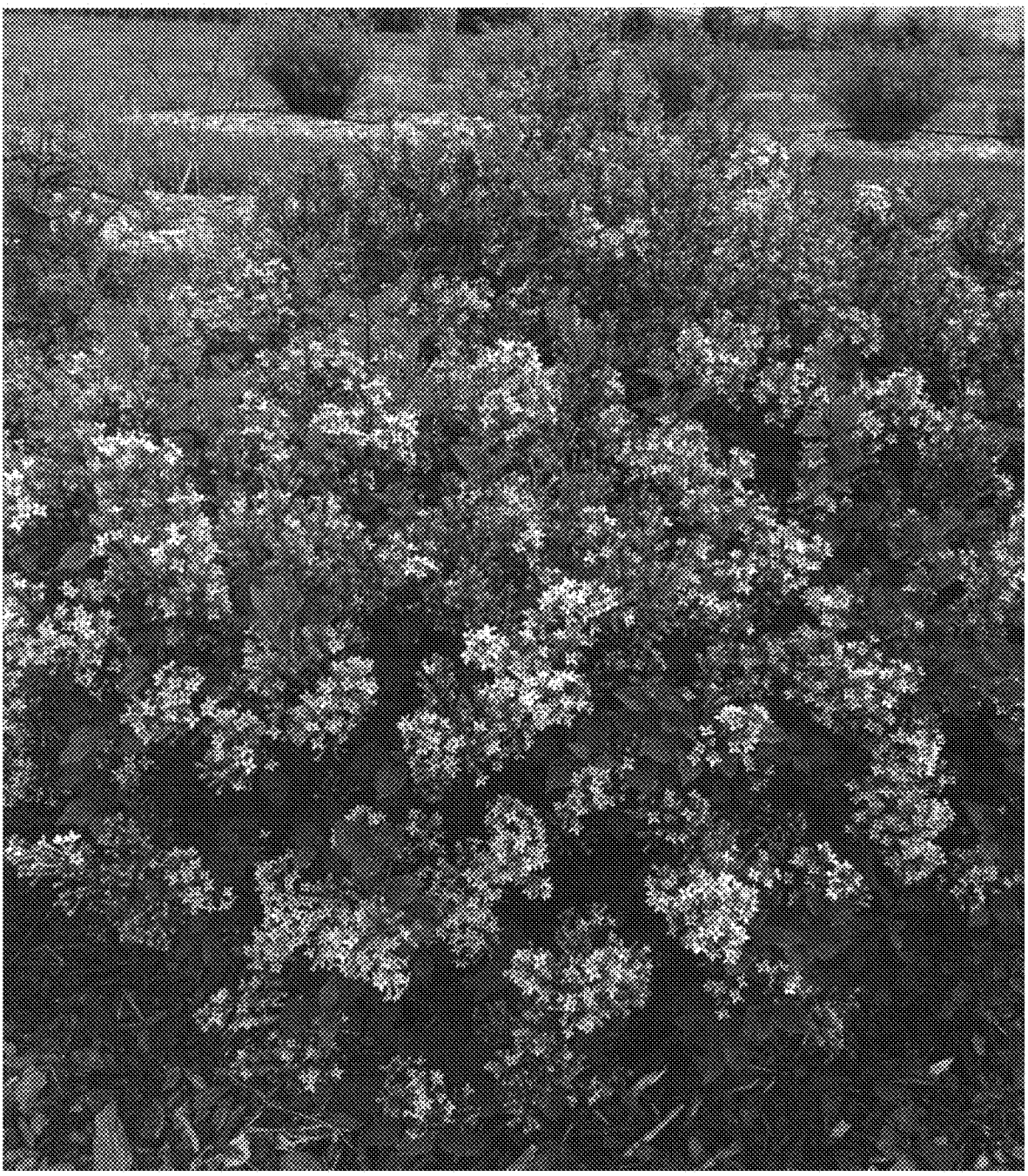
FIG. 1 shows the overall plant habit of a single bush of 'GARlisabzar'.
Figure 2:
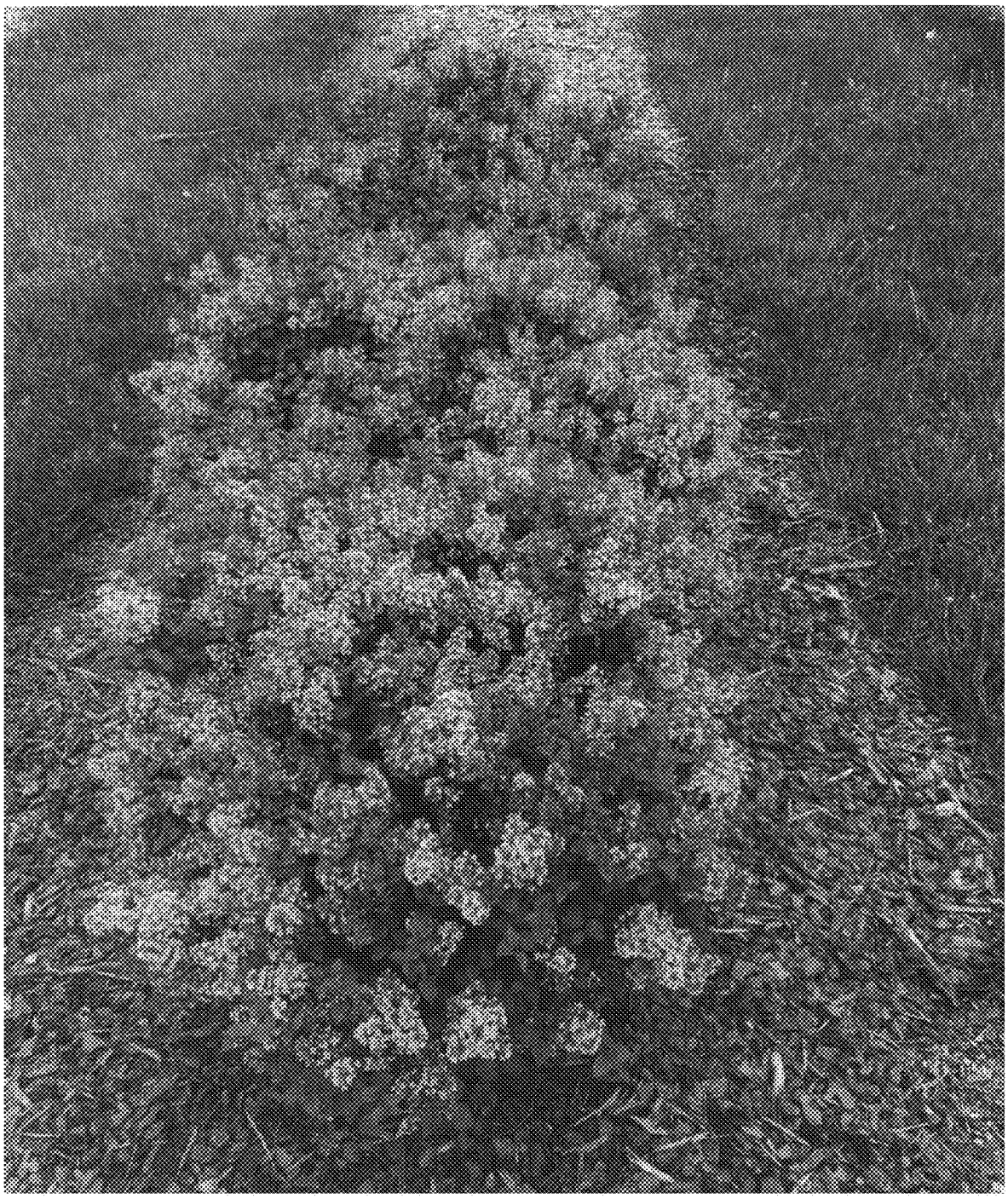
FIG. 2 shows the overall plant habit of a row of bushes of 'GARlisabzar'.
Figure 3:
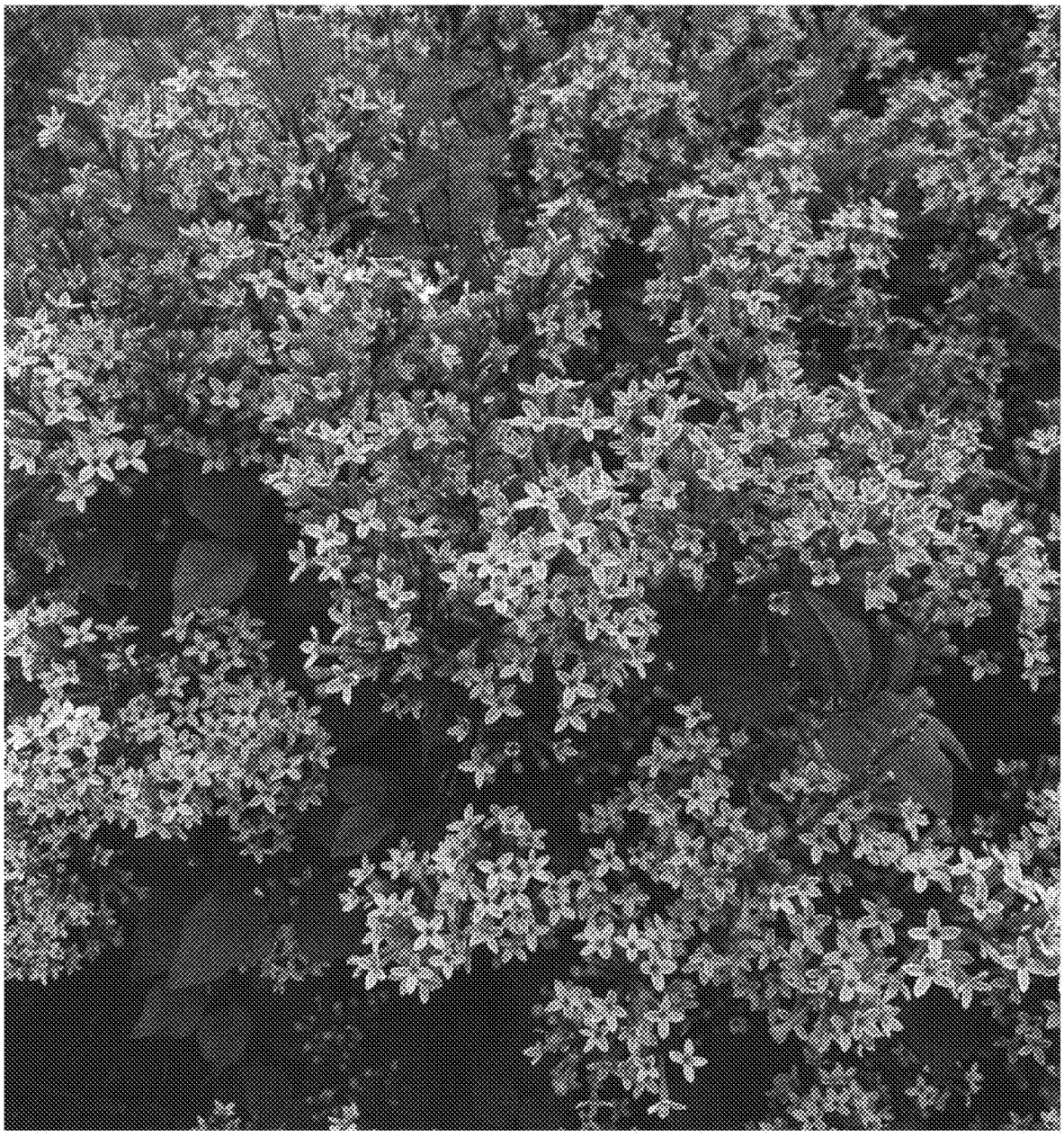
FIG. 3 shows a close-up of the individual flowers, buds, foliage, and bark of the plant.
Figure 4:
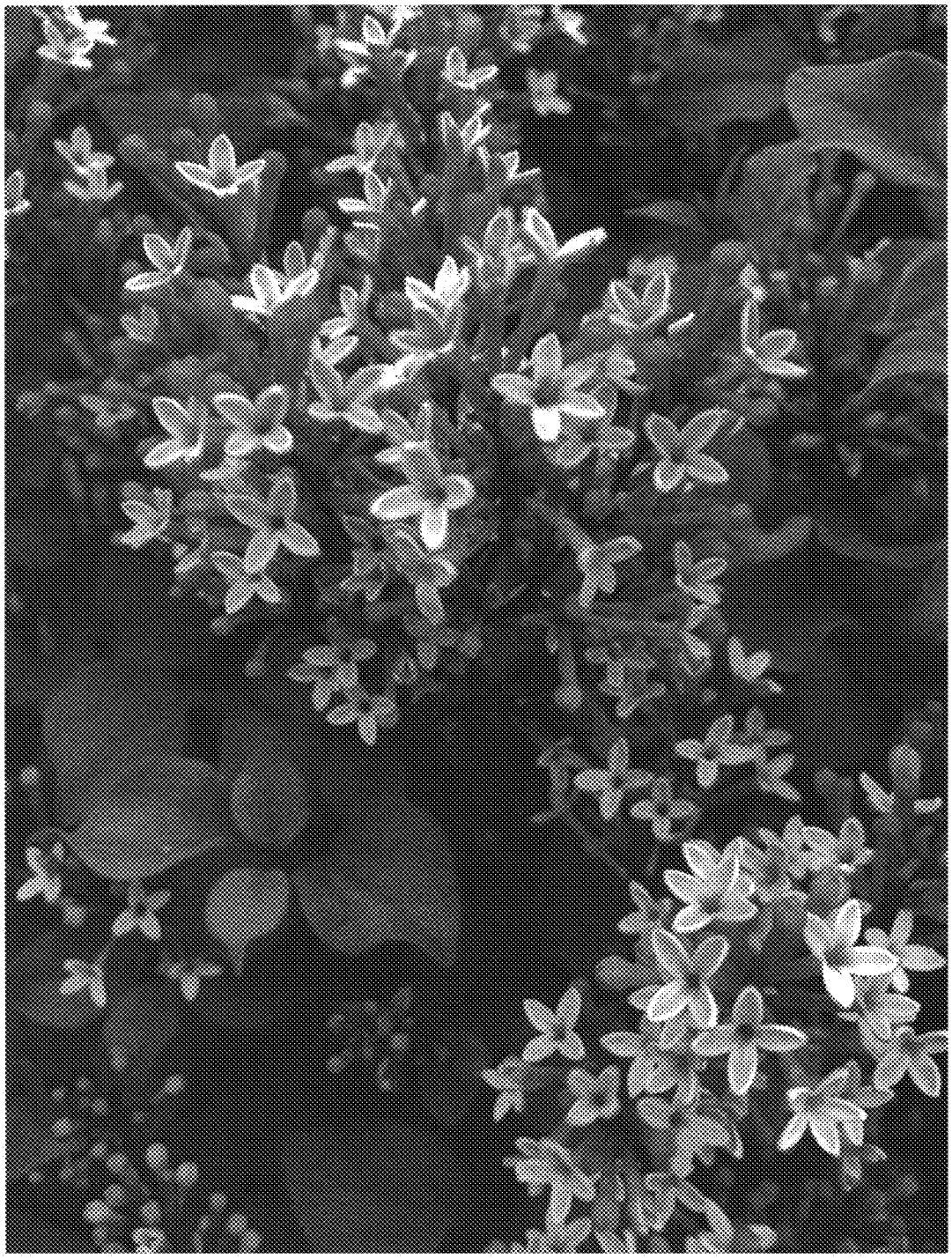
FIG. 4 shows a greater close-up of the individual flowers and buds of the plant.

The following detailed descriptions set forth the distinctive characteristics of 'GARlisabzar'. The data which define these characteristics were collected outdoors in Tipp City, Ohio in May 2015 from a 4-year-old plant. The phenotype of this new variety will vary somewhat with variation in environmental, climatic, and cultural conditions as it has not been tested in other environments. Color references are to The R.H.S. Colour Chart of The Royal Horticultural Society of London (R.H.S.) 2001.

Classification:
- *Family.*—Oleaceae.
- *Species.*—*Syringa hybrida.*
- *Common name.*—Lilac.
- *Variety.*—'GARlisabzar'.

Parentage:
- *Female parent.*—'Josee' (unpatented).
- *Male parent.*—'Bailsugar' (U.S. Plant Pat. No. 15,588).

Propagation:
- *Type.*—Softwood cuttings.
- *Time to initiate roots.*—In the summer, 18 to 21 days.
- *Time to produce a rooted young plant.*—In the summer, 12 to 16 weeks.
- *Root description.*—Fibrous.
- *Rooting habit.*—Well-branched and dense.

Plant description:

*Plant form and growth habit*.—Upright, compact, rounded and dense.

*Branching habit*.—Well-branched.

*Plant height*.—90 cm to 110 cm.

*Plant diameter* (*area of spread*).—75 cm to 90 cm.

Lateral branch description:

*Habit and number per plant*.—Very freely branching; ranging from about 11 to 14.

*Length*.—15 cm to 20 cm.

*Diameter*.—2 mm to 3 mm.

*Internode length*.—3.5 cm to 4.0 cm.

*Aspect*.—Straight.

*Strength*.—Strong.

*Texture, immature*.—Finely pubescent.

*Texture, mature*.—Finely pubescent.

*Color, immature*.—RHS 166A.

*Color, mature*.—RHS N200B.

Leaf:

*Arrangement*.—Opposite, simple.

*Length*.—2.5 cm.

*Width*.—2.0 cm.

*Shape*.—Elliptic-ovate.

*Apex*.—Acute.

*Base*.—Rounded.

*Margin*.—Entire.

*Texture*.—Upper surface: Smooth. Lower surface: Smooth mid-rib vein prominent.

*Venation pattern*.—Pinnate.

*Venation color*.—Upper surface: RHS 137B. Lower surface: RHS 138B.

*Immature leaf color*.—Upper surface: RHS 137C. Lower surface: RHS 146D.

*Mature leaf color*.—Upper surface: RHS 137B. Lower surface: RHS 138B.

*Petioles*.—Length: 8.0 mm to 9.0 mm. Diameter: 1.0 mm. Color: RHS 183A. Texture: Smooth.

Flower:

*Flower arrangement and flowering habit*.—Single, salverform, dense, packed in panicles of up to 350 flowers.

*Natural flowering season and flower longevity*.—Mid-spring, 2 to 3 weeks depending on weather.

*Fragrance*.—Very strong lilac scent.

*Inflorescence height*.—Average is 10.0 cm.

*Inflorescence diameter*.—Average is 8.0 cm.

*Flower diameter*.—5.0 mm.

*Flower length*.—12.0 mm to 13.0 mm.

*Flower buds*.—3.0 mm in diameter, 10.0 mm to 11.0 mm long.

*Flower bud shape*.—Obovate.

*Flower bud color*.—RHS 37A.

*Flower bud texture*.—Thick.

Petals:

*Quantity*.—Tubular with 4 petal lobes.

*Lobe length*.—3.0 mm.

*Lobe width*.—2.0 mm.

*Lobe shape*.—Funnelform.

*Apex*.—Rounded.

*Base*.—Fused.

*Margin*.—Entire.

*Texture*.—Upper surface: Smooth, glabrous. Lower surface: Smooth, glabrous.

*Color*.—Upper surface: RHS 73D with RHS 69C to RHS 69D edges. Lower surface: RHS 67A.

*Flower tube*.—Length: 8.0 mm to 9.0 mm. Diameter: 1.0 mm. Texture: Smooth. Color: Inner surface is RHS 67B and outer surface is RHS 67A.

*Flower throat*.—Diameter: 2.0 mm to 2.3 mm. Texture: Smooth. Color: RHS 67A.

Sepals:

*Quantity and appearance*.—There are four very small and inconspicuous sepals that are about 1.0 mm by 1.0 mm in size.

*Length*.—0.8 mm.

*Width*.—0.7 mm.

*Shape*.—Lanceolate.

*Apex*.—Acute.

*Base*.—Fused.

*Margin*.—Entire.

*Color* (*both upper and lower surfaces*).—RHS 183A.

Peduncles:

*Length*.—7.0 cm.

*Diameter*.—4.0 mm.

*Strength*.—Strong, flexible.

*Aspect*.—Straight.

*Texture*.—Smooth, finely glabrous.

*Color*.—RHS N200B.

Pedicels:

*Length*.—2.0 mm to 3.0 mm.

*Diameter*.—1.0 mm.

*Strength*.—Strong.

*Aspect*.—Straight.

*Texture*.—Smooth, glabrous.

*Color*.—RHS N187A.

Reproductive organs:

*Androecium*.—Quantity of stamens per flower: 2. Anther shape: Oblong. Anther length: 3.0 mm to 4.0 mm. Anther color: RHS 79C to RHS 79D. Amount of pollen: Little to none. Pollen color: RHS 166D.

*Gyneocium*.—Quantity of pistils per flower: 1. Pistil Length: 3.0 mm. Style length: 1.0 mm. Style color: RHS N155D. Stigma color: RHS N155B. Stigma shape: Rounded. Ovary color: RHS N155D.

Fruit and seed set: None observed.

Disease and insect resistance: Resistant to lilac powdery mildew *Erysiphe syringae* (formerly *Microsphaera syringae* and *Phyllactinia syringae*).

COMPARISON WITH PARENTAL AND COMMERCIAL LINES

Table 1 shows a comparison of differences between 'GARlisabzar' and both parental lines.

TABLE 1

Comparison with Parental Lines

| Characteristic | 'GARlisabzar' | Female parent 'Josee' | Male parent 'Bailsugar' |
|---|---|---|---|
| Plant height | 90 cm to 110 cm | 180 cm | 100 cm |
| Plant diameter | 75 cm to 90 cm | 150 cm | 90 cm |
| Flower color, upper surface | RHS 73D with RHS 69C to RHS 69D edges | RHS 69A | RHS 70C |

Table 2 shows a comparison of the differences between 'GARlisabzar' and the commercial Lilac variety 'Penda' (U.S. Plant Pat. No. 20,575).

TABLE 2

Comparison with Commercial Lines

| Characteristic | 'GARlisabzar' | 'Penda' |
|---|---|---|
| Flower color, upper surface | RHS 73D with RHS 69C to RHS 69D edges | RHS 77B |
| Flower color, lower surface | RHS 67A | RHS 77A |

TABLE 2-continued

Comparison with Commercial Lines

| Characteristic | 'GARlisabzar' | 'Penda' |
|---|---|---|
| Plant height | 90 cm to 110 cm | 100 cm |
| Plant diameter | 75 cm to 90 cm | 150 cm |

We claim:

1. A new and distinct variety of lilac plant designated 'GARlisabzar' as illustrated and described herein.

* * * * *